(12) United States Patent
Suzuki et al.

(10) Patent No.: US 10,036,706 B2
(45) Date of Patent: Jul. 31, 2018

(54) SPECTROMETRY DEVICE AND SPECTROMETRY METHOD

(71) Applicant: HAMAMATSU PHOTONICS K.K., Hamamatsu-shi, Shizuoka (JP)

(72) Inventors: Kengo Suzuki, Hamamatsu (JP); Kazuya Iguchi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/531,875

(22) PCT Filed: Nov. 19, 2015

(86) PCT No.: PCT/JP2015/082604
§ 371 (c)(1),
(2) Date: May 31, 2017

(87) PCT Pub. No.: WO2016/088574
PCT Pub. Date: Jun. 9, 2016

(65) Prior Publication Data
US 2017/0284939 A1    Oct. 5, 2017

(30) Foreign Application Priority Data

Dec. 2, 2014    (JP) ................. 2014-243643

(51) Int. Cl.
*G01N 21/64*    (2006.01)

(52) U.S. Cl.
CPC ... *G01N 21/645* (2013.01); *G01N 2021/6417* (2013.01); *G01N 2021/6471* (2013.01); *G01N 2201/08* (2013.01)

(58) Field of Classification Search
CPC ......... G01N 21/645; G01N 2021/6417; G01N 2021/6471; G01N 2201/08
See application file for complete search history.

(56) References Cited

FOREIGN PATENT DOCUMENTS

| JP | H09-292281 A | 11/1997 |
|---|---|---|
| JP | 2010-151632 A | 7/2010 |

(Continued)

OTHER PUBLICATIONS

International Preliminary Report on Patentability dated Jun. 6, 2017 for PCT/JP2015/082604.

(Continued)

*Primary Examiner* — Mark R Gaworecki
(74) *Attorney, Agent, or Firm* — Drinker Biddle & Reath LLP (57) ABSTRACT

A spectroscopic measurement apparatus includes a light source, an integrator, a spectroscopic detector, and an analysis unit. The integrator includes an internal space in which a measurement object is disposed, a light input portion for inputting light to the internal space, a light output portion for outputting light from the internal space, a sample attachment portion for attaching the measurement object, and a filter attachment portion for attaching a filter unit. The filter unit has a transmission spectrum in which an attenuation rate for excitation light is larger than an attenuation rate for up-conversion light, and attenuates the light output from the light output portion. The analysis unit analyzes luminous efficiency of the measurement object on the basis of the transmission spectrum data and the spectroscopic spectrum data acquired by the spectroscopic detector.

18 Claims, 6 Drawing Sheets

(56) References Cited

FOREIGN PATENT DOCUMENTS

JP          2011-196735 A      10/2011
WO     WO-2014/119038 A1      8/2014

OTHER PUBLICATIONS

Askes, S H C, et al., "Activation of a Photodissociative Ruthenium Complex by Triplet-Triplet Annihilation Upconversion in Liposomes", Angewandte Chemie International Edition, vol. 53 (Supporting Information p. 1-8), Dec. 11, 2013, p. 1029-p. 1033.
Horigome, Jun et al., "A Simple Correction Method for Determination of Absolute Fluorescence Quantum Yields of Solid Samples with a Conventional Fluorescence Spectrophotometer", Bunseki Kagaku, vol. 58, No. 6, Jun. 2009, p. 553-p. 559.
Page, R H, et al., "Upconversion-pumped luminescence efficiency of rare-earth-doped hosts sensitized with trivalent ytterbium", J. Opt. Soc. Am. B, vol. 15, No. 3, Mar. 1998, p. 996-p. 1008.
Nadort, Annemarie, et al., "Quantitative Imaging of Single Upconversion Nanoparticles in Biological Tissue", PLOS ONE, vol. 8, No. 5, May 14, 2013, p. e63292, XP055470603.
Askes, Sven, H.C., et al., "Activation of a Photodissociative Ruthenium Complex by Triplet-Triplet Annihilation Upconversion in Liposomes", Angewandte Chemie International Edition, vol. 53, No. 4, Jan. 20, 2014, p. 1029-p. 1033, XP055344167.
Wang, Junxin, et al., "Photon energy upconversion through thermal radiation with the power efficiency reaching 16%", Nature Communications, vol. 5, Nov. 28, 2014, p. 5669, XP055470784.
Boyer, John-Christopher, et al., "Absolute quantum yield measurements of colloidal $NaYF_4$ : $Er^{3+}$, $Yb^{3+}$ upconverting nanoparticles", Nanoscale, May 29, 2010, p. 1417, XP055470550.
Greenham, N. C., et al., "Measurement of absolute photoluminescence quantum efficiencies in conjugated polymers", Chemical Physics Letters, 1995, p. 89-p. 96, XP002079651.

SPECTROMETRY DEVICE AND SPECTROMETRY METHOD

TECHNICAL FIELD

An aspect of the present invention relates to a spectroscopic measurement apparatus and a spectroscopic measurement method.

BACKGROUND ART

Spectroscopic measurement techniques for measuring light emission efficiency and the like of a measurement object with an integrator and a spectroscopic detector have been known. The integrator includes an internal space in which the measurement object is disposed, a light input portion for inputting the light output from a light source into the internal space, and a light output portion for outputting the measurement target light from the internal space to the outside. The internal space of the integrator is, for example, spherical, and covered with an inner wall surface having high reflectance and excellent diffuseness. Alternatively, the internal space of the integrator is, for example, hemispherical, and in this case, an inner wall of a hemispherical portion has a wall surface with high reflectance and excellent diffuseness and a planar portion is a flat mirror with high reflectance.

In the integrator, excitation light output from the light source can be input from the light input portion into the internal space, and the excitation light can be diffused and reflected multiple times in the internal space. In addition, in the integrator, emission light (such as fluorescence), generated when the measurement object disposed in the internal space is irradiated with the excitation light, can also be diffused and reflected multiple times in the internal space. Then, the integrator outputs the measurement target light from the internal space to the outside through the light output portion. The measurement target light is the excitation light and/or the emission light.

The spectroscopic detector disperses the measurement target light output from the integrator to the outside, and acquires spectrum data. The spectroscopic detector disperses the measurement target light into respective wavelength components through a spectroscopic element such as a grating or a prism, and detects the intensity of the dispersed light of each wavelength using an optical sensor. The optical sensor has a plurality of light receiving portions arrayed one-dimensionally, and by detecting the light intensity of the wavelength component by the light receiving portion corresponding to each wavelength, the spectrum data of the measurement target light can be acquired. Then, by analyzing the spectrum data, the luminous efficiency and the like of the measurement object can be measured without depending on the angle characteristic and the like of the light emission of the measurement object.

In the spectroscopic measurement technique using the integrator, the measurement object may be the organic EL (electroluminescence) material or the fluorescent material. The measurement object may be in the arbitrary form, such as a solution, a thin film, or powder. For such a measurement object, evaluation of the photoluminescence quantum yield (internal quantum efficiency) is important. The photoluminescence quantum yield refers to the ratio of the number of photons of the emission light generated in the measurement object to the number of photons of the excitation light absorbed by the measurement object. The spectroscopic measurement technique using the integrator is preferably applicable for evaluating the photoluminescence quantum yield of the measurement object.

The up-conversion luminescence material has been researched using such a spectroscopic measurement technique (see Non Patent Document 1). In the up-conversion luminescence phenomenon, the light (up-conversion light) having a shorter wavelength than the excitation light is generated. The up-conversion occurs in the non-linear optical phenomenon such as the multiphoton absorption and the second-order or third-order harmonic generation, the multistage excitation phenomenon of the rare-earth element, the phenomenon based on the triplet-triplet annihilation (TTA), or the like.

In the spectroscopic measurement technique described in Non Patent Document 1, the luminous efficiency of the up-conversion luminescence material which is the measurement object is measured by disposing a filter, having a transmission characteristic that is different in excitation light measurement and up-conversion light measurement, on an optical path between the integrator and the spectroscopic detector.

CITATION LIST

Non Patent Literature

Non Patent Document 1: Sven H. C. Askes et al., "Activation of a Photodissociative Ruthenium Complex by Triplet-Triplet Annihilation Upconversion in Liposomes", Angewandte Chemie International Edition, Volume 53 Issue 4(2014) pp. 1029-1033

SUMMARY OF INVENTION

Technical Problem

The present inventors have found out that the measurement of the luminous efficiency of the up-conversion light has a problem as below.

In order to generate the up-conversion light, it is necessary to increase the intensity density of the excitation light with which the measurement object is irradiated. Here, the luminous efficiency of the up-conversion light is low, and therefore, in the case of performing the evaluation of the photoluminescence quantum yield (internal quantum efficiency) in which both the intensity of the absorbed excitation light and the intensity of the up-conversion light need to be acquired, the spectroscopic detector is possibly saturated because of the excitation light with the high intensity, and in this case, it may be impossible to calculate the photoluminescence quantum yield and the like.

Further, some of the up-conversion luminescence materials have higher photoluminescence quantum yield when irradiated with the excitation light having the higher intensity density. In those materials, the spectroscopic detector is possibly saturated due to the up-conversion light having the high intensity, and in this case, it may be impossible to evaluate the photoluminescence quantum yield and the like.

The technique for measuring the luminous efficiency of the up-conversion light described in Non Patent Literature 1 may solve such a problem. However, in the excitation light measurement and the up-conversion light measurement, it is necessary to change and dispose the filters with the different transmission characteristics on the optical path between the integrator and the spectroscopic detector, and therefore, the light output from the integrator cannot be measured by the spectroscopic detector at one time, and it takes effort and long time to perform the measurement. Further, since the measurement condition is different in the excitation light measurement and the up-conversion light measurement, the accuracy of measuring the luminous efficiency of the measurement object may deteriorate.

One aspect of the present invention has been made in order to solve the above problem, and an object thereof is to provide a spectroscopic measurement apparatus and a spectroscopic measurement method that can easily measure the generation efficiency of the up-conversion light.

Solution to Problem

A spectroscopic measurement apparatus according to one aspect of the present invention is an apparatus for measuring luminous efficiency of a measurement object which outputs up-conversion light by input of excitation light, and the apparatus includes (1) an integrator including an internal space in which the measurement object is disposed, a light input portion for inputting the excitation light from outside to the internal space, and a light output portion for outputting light from the internal space to the outside; (2) a filter unit having a transmission spectrum in which an attenuation rate for the excitation light is larger than an attenuation rate for the up-conversion light, and for attenuating the light output from the light output portion in accordance with the transmission spectrum; (3) a spectroscopic detector for dispersing the light attenuated and output by the filter unit, and acquiring spectroscopic spectrum data; and (4) an analysis unit for analyzing the luminous efficiency of the measurement object on the basis of the transmission spectrum data and the spectroscopic spectrum data.

A spectroscopic measurement method according to one aspect of the present invention is a method for measuring luminous efficiency of a measurement object which outputs up-conversion light by input of excitation light using an integrator including an internal space in which the measurement object is disposed, a light input portion for inputting the excitation light from outside to the internal space, and a light output portion for outputting light from the internal space to the outside, and (1) using the integrator including the internal space in which the measurement object is disposed, the light input portion for inputting the excitation light from the outside to the internal space, and the light output portion for outputting the light from the internal space to the outside, and the method includes (2) inputting the excitation light from the light input portion of the integrator to the internal space; (3) attenuating the light output from the light output portion in accordance with a transmission spectrum by a filter unit having the transmission spectrum in which an attenuation rate for the excitation light is larger than an attenuation rate for the up-conversion light; (4) dispersing the light attenuated and output by the filter unit and acquiring spectroscopic spectrum data by a spectroscopic detector; and (5) analyzing the luminous efficiency of the measurement object on the basis of the transmission spectrum data and the spectroscopic spectrum data by an analysis unit.

Advantageous Effects of Invention

According to one aspect of the present invention, the generation efficiency of the up-conversion light can be measured easily.

DESCRIPTION OF EMBODIMENTS

Hereinafter, embodiments for carrying out the present invention will be described in detail with reference to the accompanying drawings. In the description of the drawings, the same elements will be denoted by the same reference signs, without redundant description. The present invention is not limited to these examples, and it is intended that the present invention includes all the changes within an equivalent meaning and range to the claims indicated in the claims.

Figure 1:
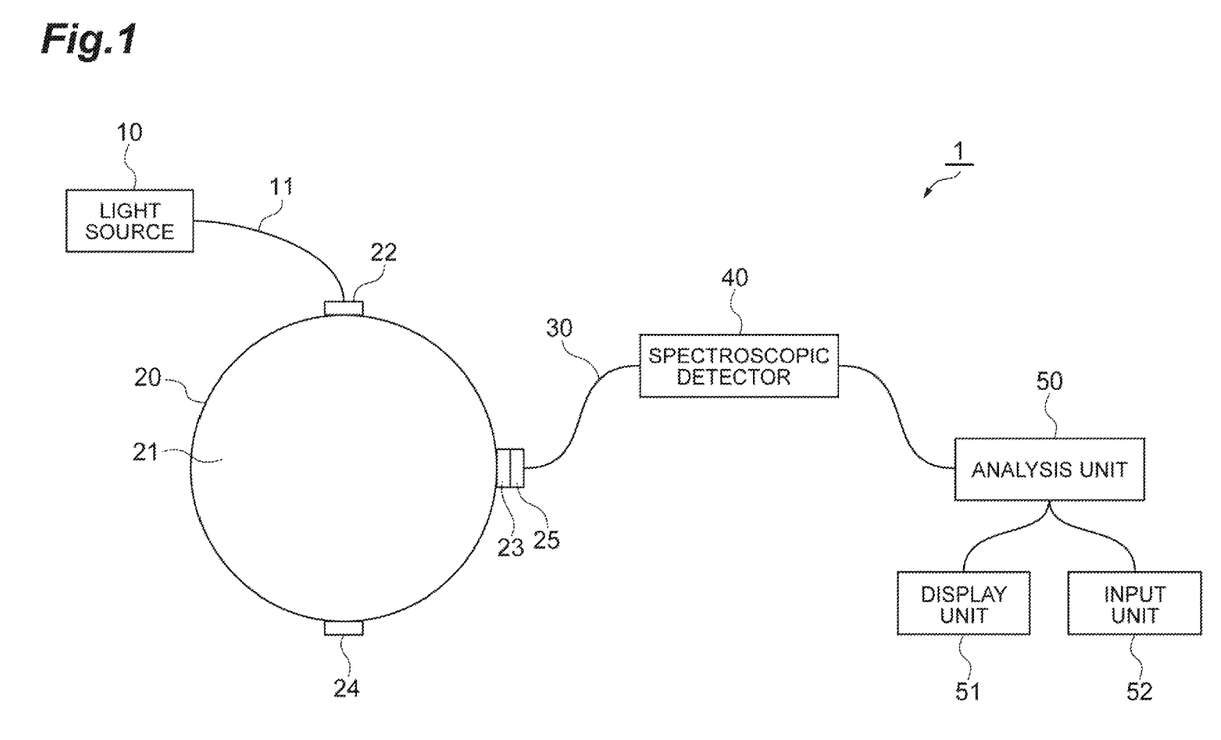
FIG. 1 is a diagram illustrating a configuration of a spectroscopic measurement apparatus 1.

FIG. 1 is a diagram illustrating a configuration of a spectroscopic measurement apparatus 1. The spectroscopic measurement apparatus 1 includes a light source 10, an input light guide 11, an integrator 20, an output light guide 30, a spectroscopic detector 40, an analysis unit 50, a display unit 51, and an input unit 52.

The light source 10 outputs light to be input to an internal space 21 of the integrator 20. The light output from the light source 10 includes, for example, standard light having a known spectrum for calibrating the sensitivity of the entire apparatus, and excitation light with which the measurement object disposed in the internal space 21 of the integrator 20 is irradiated. The excitation light output from the light source 10 has the wavelength that can produce the up-conversion luminescence phenomenon in the measurement object. The wavelength of the light output from the light source 10 may be variable. The light source 10 is, for example, a laser diode that outputs laser light with a wavelength of 980 nm. Further, the light source 10 may include an ND filter or a relay optical system. The input light guide 11 guides the light output from the light source 10 to a light input portion 22 of the integrator 20.

The integrator (optical integrator) 20 includes the internal space 21 in which the measurement object is optically disposed, the light input portion 22 for inputting the light (input light) output from the light source 10 and guided by the input light guide 11 into the internal space 21, a light output portion 23 for outputting the light (output light) from the internal space 21 to the outside, a sample attachment portion 24 for attaching the measurement object, and a filter attachment portion 25 for attaching a filter unit. The internal space 21 is spherical and is covered with an inner wall surface having high reflectance and excellent diffuseness. The sample attachment portion 24 disposes the measurement object at a position where the light input to the internal space 21 through the light input portion 22 is incident. The filter attachment portion 25 is provided for the light output portion 23, and disposes the filter unit that attenuates the light output from the light output portion 23.

In the integrator 20, the light output from the light source 10 can be input from the light input portion 22 into the internal space 21 and the light can be diffused and reflected multiple times in the internal space 21. Further, in the integrator 20, the emission light (in the present embodiment, up-conversion light) generated in the measurement object disposed in the internal space 21 can also be diffused and reflected multiple times in the internal space 21. Then, the integrator 20 outputs the measurement target light from the internal space 21 to the outside through the light output portion 23. The measurement target light is the light input from the light source 10 to the internal space 21 and/or the up-conversion light generated in the measurement object.

To the sample attachment portion 24, a sample container for holding the measurement object that outputs the up-conversion light by input of the excitation light is attached. For example, when the measurement object is liquid, a solution sample cell including a transparent material that transmits light (for example, quartz glass or plastic) is attached to the sample attachment portion 24 as the sample container. When the measurement object is solid like powder or a thin film, a solid sample cell or a solid sample container including a transparent material that transmits light (for example, quartz glass or plastic) or metal is attached to the sample attachment portion 24 as the sample container.

Here, the measurement object may be disposed entirely within the internal space 21 of the integrator 20, or a part of the measurement object may be disposed in the internal space 21 of the integrator 20. Using an optical attachment attached to the sample attachment portion 24, the sample disposed outside the inner wall of the integrator 20 may be optically disposed in the internal space 21 of the integrator 20.

The output light guide 30 guides the light, which is output from the light output portion 23 of the integrator 20 and attenuated by the filter unit, to the spectroscopic detector 40. The spectroscopic detector 40 receives the light guided by the output light guide 30, disperses the light, and acquires spectrum data. The spectroscopic detector 40 disperses the input light into respective wavelength components through a spectroscopic element such as a grating or a prism, and detects the intensity of the dispersed light with each wavelength using an optical sensor. The optical sensor has a plurality of light receiving portions arrayed one-dimensionally, and by detecting the light intensity of the wavelength component by the light receiving portion corresponding to each wavelength, the spectrum data of the measurement target light can be acquired.

For example, the optical sensor of the spectroscopic detector 40 is a CCD linear image sensor or a CMOS linear image sensor formed on a silicon substrate, and is sensitive to light of a wavelength of 350 nm to 1100 nm. Further, for example, the optical sensor of the spectroscopic detector 40 is an InGaAs linear image sensor, and is sensitive to light of a wavelength of 900 nm to 1650 nm. It is preferable that the measurement time (exposure time) of the spectroscopic detector 40 can be variably set and that the exposure time is set appropriately in accordance with the sensitivity of the optical sensor.

To the analysis unit (analyzer) 50, the spectrum data acquired by the spectroscopic detector 40 is input, and the analysis unit analyzes the spectrum data. The analyzing process will be described later. The analysis unit 50 includes a storage unit (storage) that stores the input spectrum data, the analysis results, and the like. The analysis unit 50 may control the light source 10 and the spectroscopic detector 40. The analysis unit 50 is a computer including a processor and a memory. The analysis unit 50 uses the processor to execute various analysis and controls. Such a computer corresponds to, for example, a personal computer or a tablet terminal. The analysis unit 50 can be integrated with the display unit 51 and the input unit 52.

The display unit (display) 51 displays the spectrum data input by the analysis unit 50, and also displays the analysis results by the analysis unit 50. The input unit 52 corresponds to, for example, a keyboard or a mouse, accepts the input instruction from an operator who performs the spectroscopic measurement using the spectroscopic measurement apparatus 1, and sends the input information (for example, measurement condition or display condition) to the analysis unit 50.

Figure 2:
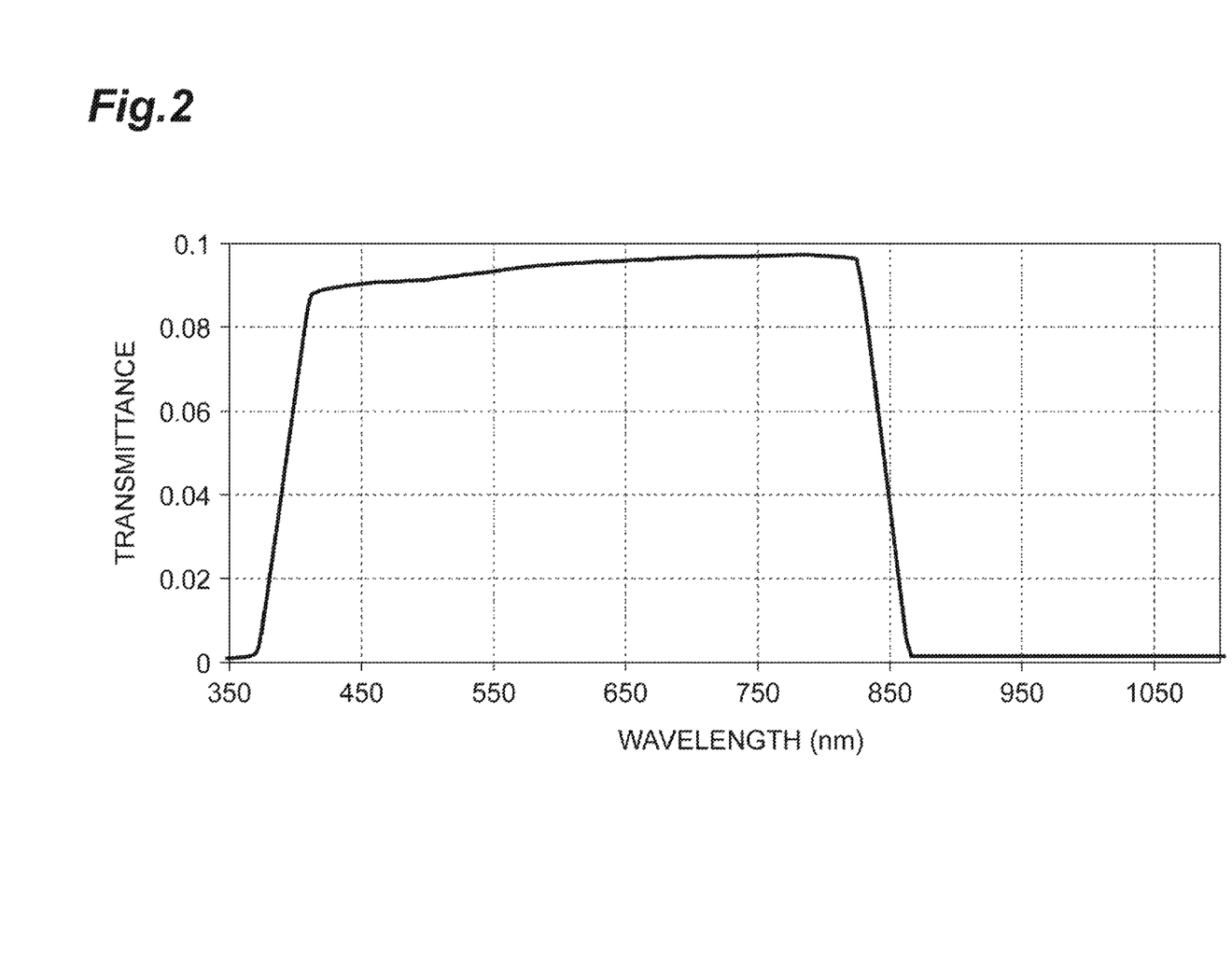
FIG. 2 is a diagram illustrating an example of a transmission spectrum of a filter unit attached to a filter attachment portion 25 of an integrator 20.

FIG. 2 is a diagram illustrating an example of a transmission spectrum of the filter unit attached to the filter attachment portion 25 of the integrator 20. In the transmission characteristic of the filter unit, the attenuation rate in the excitation light wavelength region (wavelength region including 980 nm) is larger than the attenuation rate in the up-conversion light wavelength region. In accordance with such a transmission spectrum, the filter unit attenuates the light output from the light output portion 23. This filter unit may include, for example, a first filter for selectively attenuating the excitation light on the long-wavelength side out of the excitation light and the up-conversion light, and a second filter for attenuating both the excitation light and the up-conversion light.

The first filter may be a short-pass filter or a band-pass filter. The second filter may be an ND filter or may be formed of a light-reflective material. In the latter case, the light-reflective material may be Spectralon (registered trademark), which is the material with high reflectance and excellent diffuseness to be provided for the inner wall surface of the integrator 20. Spectralon has approximately constant reflectance over a wide wavelength region from the visible range to the near-infrared range. A Spectralon filter formed by a sheet of Spectralon can be used as the second filter. Such a Spectralon filter can be used not only as the second filter but also as a part of the inner wall surface of the integrator 20 that diffuses and reflects the light. That is, the second filter may be formed of the same material as the light-reflective material provided for the inner wall surface of the integrator 20.

Figure 3:
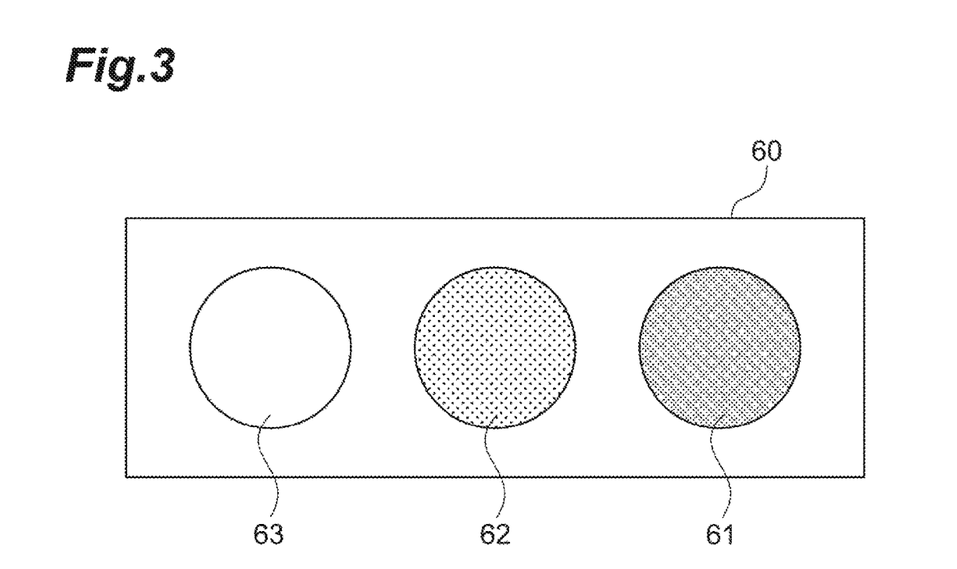
FIG. 3 is a diagram illustrating an example of a filter set 60 attached to the filter attachment portion 25 of the integrator 20.

In the filter attachment portion 25 of the integrator 20, the filter is preferably replaceable freely on the optical path with the filter unit having the transmission spectrum as illustrated in FIG. 2, or a filter having another transmission spectrum. FIG. 3 is a diagram illustrating an example of a filter set 60 attached to the filter attachment portion 25 of the integrator 20. This filter set 60 is formed by arranging side by side a filter unit 61 having the transmission spectrum as illustrated in FIG. 2, a short-pass filter 62 that selectively attenuates the excitation light out of the excitation light and the up-conversion light, and an opening (without filter) 63. The opening 63 or any filter can be disposed on the optical path by sliding the filter set 60 in the filter attachment portion 25. Here, the filter set 60 may have a configuration in which the filter unit 61, the short-pass filter 62, and the opening 63 are disposed on the circumference and rotated, so that the opening 63 or any filter can be disposed on the optical path.

Here, the filter attachment portion 25 and the filter set 60 may be provided for the light output portion 23 of the integrator 20, or the light input portion of the spectroscopic detector 40, as long as they are provided on the optical path between the light output portion 23 of the integrator 20 and the light input portion of the spectroscopic detector 40.

Next, the operation of the spectroscopic measurement apparatus according to the present embodiment and the spectroscopic measurement method according to the present embodiment will be described. In the spectroscopic measurement method of the present embodiment, spectroscopic measurement is performed using the spectroscopic measurement apparatus 1 described above. In the operation example of the present embodiment, the photoluminescence quantum yield of the up-conversion luminescence material which is the measurement object is obtained through the procedure in accordance with the flow of FIG. 4.

Figure 4:
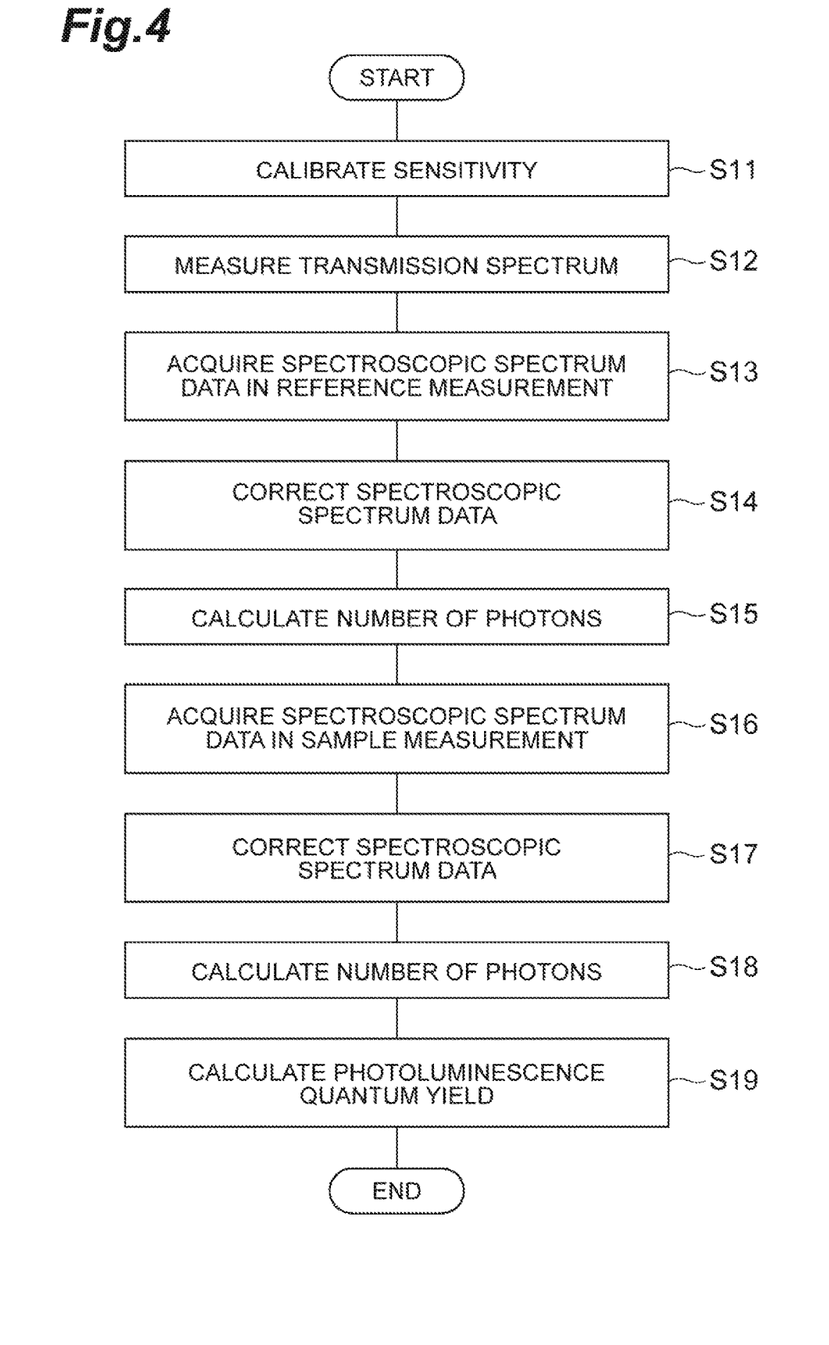
FIG. 4 is a flowchart for describing the procedure of evaluating a photoluminescence quantum yield of a measurement object.

In step S11, a standard light source is used as the light source 10, the standard light with the known spectrum is input to the integrator 20, the light output from the integrator 20 at that time is dispersed by the spectroscopic detector 40, and the spectrum is acquired, and thus, the sensitivity of the spectroscopic detector 40 is calibrated. In the subsequent steps, the spectrum after sensitivity calibration is obtained. The spectrum after sensitivity calibration is the spectrum in which the vertical axis is the number of photons and the horizontal axis is the wavelength.

In step S12, the transmission spectrum of the filter unit 61 is measured. In this state, the measurement object is not disposed in the internal space 21 of the integrator 20. In a case where the filter unit 61 or the opening (without filter) 63 is disposed on the optical path in the filter attachment portion 25, the standard light is input to the integrator 20, the light output from the integrator 20 is dispersed by the spectroscopic detector 40, and the spectrum is acquired. The spectrum data acquired by the spectroscopic detector 40 when the filter unit 61 is disposed on the optical path is $S_1(\lambda)$, the spectrum data obtained by the spectroscopic detector 40 when the opening 63 is disposed on the optical path is $S_0(\lambda)$, and assuming that the exposure time is the same, the transmission spectrum data $T(\lambda)$ of the filter unit 61 is obtained by the following Formula (1). $\lambda$ is the wavelength. The transmission spectrum data $T(\lambda)$ is stored in the storage unit of the analysis unit 50.

$$T(\lambda) = S_1(\lambda)/S_0(\lambda) \tag{1}$$

In step S13, an excitation light source is used as the light source 10, and the reference measurement is performed in a state where the measurement object is not disposed in the internal space 21 of the integrator 20. When the measurement object is disposed in the internal space 21 in a state where the object is set in a container in the sample measurement in step S16 to be described below, the container is disposed in the internal space 21 in the reference measurement in step S13. In a state where the filter unit 61 is disposed on the optical path in the filter attachment portion 25, the excitation light is input to the integrator 20. Then, the light output from the integrator 20 and transmitted through the filter unit 61 is received by the spectroscopic detector 40, and the spectroscopic spectrum data $S_{R0}(\lambda)$ is acquired.

Figure 5:
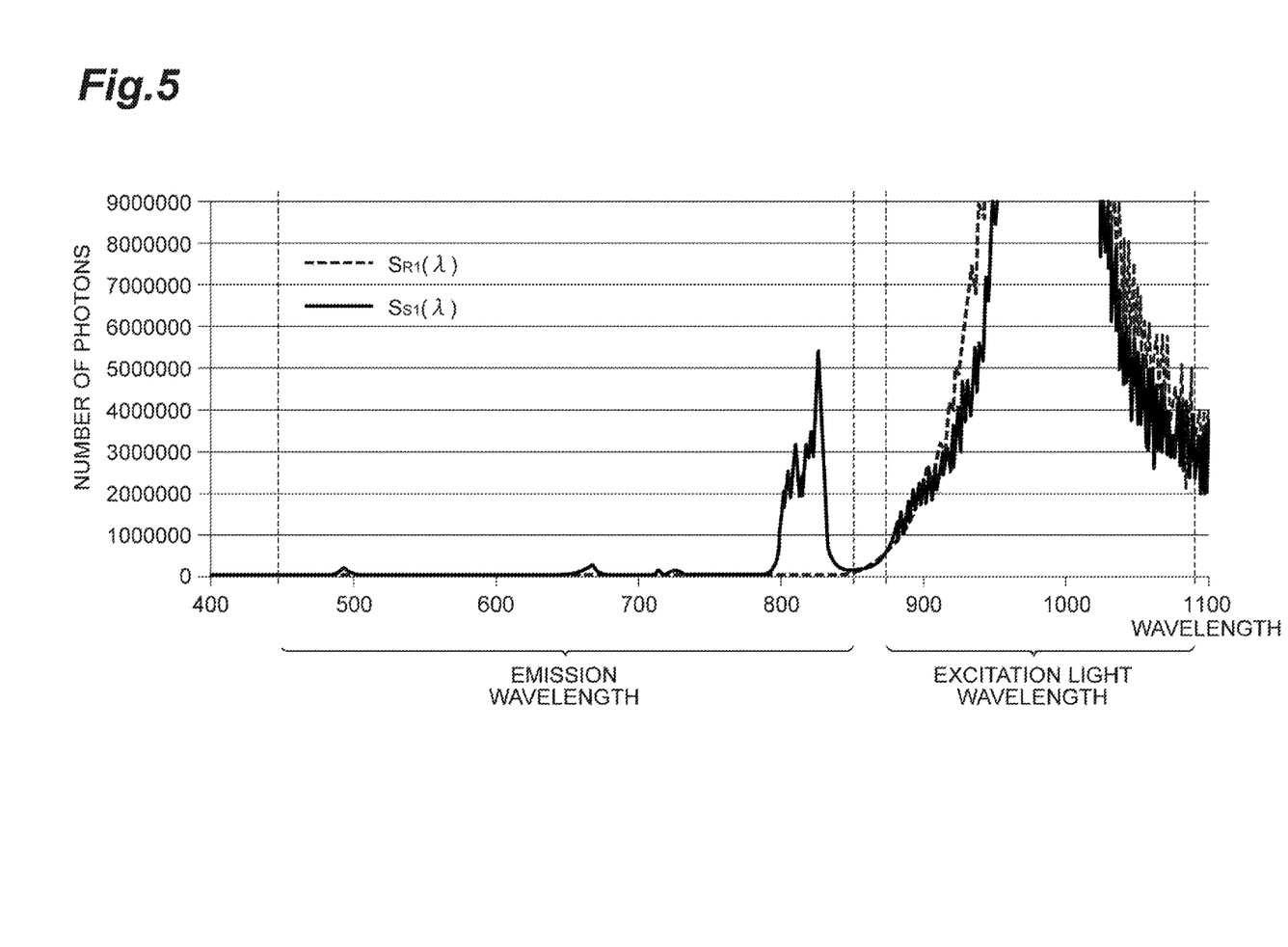
FIG. 5 is a diagram illustrating an example of a spectroscopic spectrum $S_{R1}(\lambda)$ after correction in step S14 and a spectroscopic spectrum $S_{S1}(\lambda)$ after correction in step S17.

In step S14, the analysis unit 50 obtains spectroscopic spectrum data $S_{R1}(\lambda)$ after correction (FIG. 5) by dividing the spectroscopic spectrum data $S_{R0}(\lambda)$ acquired in step S13, by the transmission spectrum data $T(\lambda)$ acquired in step S12 (Formula (2) below). The spectroscopic spectrum data $S_{R1}(\lambda)$ after correction corresponds to the spectroscopic spectrum data before attenuation by the filter unit 61.

$$S_{R1}(\lambda) = S_{R0}(\lambda)/T(\lambda) \tag{2}$$

Here, the spectroscopic spectrum data $S_{R1}(\lambda)$ after correction may be obtained by calculating the reciprocal of the transmission spectrum data $T(\lambda)$, which is acquired in step S12, as a correction coefficient $K(\lambda)$, and multiplying the spectroscopic spectrum data $S_{R0}(\lambda)$ acquired in step S13 by the correction coefficient $K(\lambda)$. Further, the correction coefficient $K(\lambda)$ may be stored in the storage unit of the analysis unit 50.

In step S15, the analysis unit 50 obtains the number of photons $I_{R1}$ in the excitation light wavelength region and the number of photons $I_{R2}$ in the up-conversion light wavelength region on the basis of the spectroscopic spectrum data $S_{R1}(\lambda)$ obtained in step S14.

The number of photons $I_{R1}$ in the excitation light wavelength region can be obtained as the integrated value of the spectroscopic spectrum data $S_{R1}(\lambda)$ in the excitation light wavelength region. The number of photons $I_{R2}$ in the up-conversion light wavelength region can be obtained as the integrated value of the spectroscopic spectrum data $S_{R1}(\lambda)$ in the up-conversion light wavelength region. The number of photons to be obtained subsequently can be similarly obtained as the integrated value of the spectrum data in a predetermined wavelength region.

In step S16, an excitation light source is used as the light source 10, and the sample measurement is performed in a state where the measurement object is disposed in the internal space 21 of the integrator 20. In a state where the filter unit 61 is disposed on the optical path in the filter attachment portion 25, the excitation light is input to the integrator 20. Then, the light output from the integrator 20 and transmitted through the filter unit 61 is received by the spectroscopic detector 40, and the spectroscopic spectrum data $S_{S0}(\lambda)$ is acquired.

In step S17, the analysis unit 50 obtains the spectroscopic spectrum data $S_{S1}(\lambda)$ after correction (FIG. 5) by dividing the spectroscopic spectrum data $S_{S0}(\lambda)$ acquired in step S16 by the transmission spectrum data $T(\lambda)$ acquired in step S12 (Formula 3 below). The spectroscopic spectrum data $S_{S1}(\lambda)$ after correction corresponds to the spectroscopic spectrum data before attenuation by the filter unit 61.

$$S_{S1}(\lambda) = S_{S0}(\mu)/T(\lambda) \tag{3}$$

Here, the spectroscopic spectrum data $S_{S1}(\lambda)$ after the correction may be obtained by multiplying the spectroscopic spectrum data $S_{S0}(\lambda)$ acquired in step S16 by the correction coefficient $K(\lambda)$.

In step S18, the analysis unit 50 obtains the number of photons $I_{S1}$ in the excitation light wavelength region and the number of photons $I_{S2}$ in the up-conversion light wavelength region on the basis of the spectroscopic spectrum data $S_{S1}(\lambda)$ obtained in step S17.

Here, the excitation light wavelength region and the up-conversion light wavelength region in steps S15 and S18 may be set by the user of the spectroscopic measurement apparatus 1 through the input unit 52 or may be automatically set by the analysis unit 50 on the basis of the spectroscopic spectrum data obtained in steps S14 and S17. The excitation light wavelength region in step S15 and the excitation light wavelength region in step S18 are the same wavelength region. The up-conversion light wavelength region in step S15 and the up-conversion light wavelength region in step S18 are the same wavelength region.

In step S19, the analysis unit 50 obtains the photoluminescence quantum yield PLQY from Formula (4) below on the basis of the number of photons $I_{R1}$ in the excitation light wavelength region and the number of photons $I_{R2}$ in the up-conversion light wavelength region obtained in step S15, and the number of photons $I_{S1}$ in the excitation light wavelength region and the number of photons $I_{S2}$ in the up-conversion light wavelength region obtained in step S18. The analysis unit 50 can obtain the external quantum efficiency by multiplying the absorptance of the measurement object and the internal quantum yield PLQY.

$$PLQY = (I_{S2} - I_{R2})/(I_{R1} - I_{S1}) \qquad (4)$$

Here, the order of step S12 (transmission spectrum measurement), step S13 (reference measurement), and step S16 (sample measurement) is arbitrary. However, when steps S13 and S16 are performed after the spectrum data $S_1(\lambda)$ is acquired in a state where the filter unit 61 is disposed on the optical path in step S12, the filter unit 61 may be left disposed on the optical path, and thus, the easy measurement can be performed under the same measurement condition.

Steps S11 and S12 may be performed before the spectroscopic measurement apparatus 1 is shipped from the factory, while steps S13 to S19 may be performed by the user of the spectroscopic measurement apparatus 1 after the shipment. The results obtained from steps S11 and S12 may be used in every measurement performed thereafter. Steps S11 and S12 may be performed every time prior to steps S13 to S19.

In this embodiment, in both the reference measurement and the sample measurement, the excitation light and the up-conversion light output from the integrator 20 are attenuated by the same filter unit 61 appropriately and input to the spectroscopic detector 40, and based on the spectroscopic spectrum data acquired by the spectroscopic detector 40, the number of photons in the excitation light wavelength region and the number of photons in the up-conversion light wavelength region are obtained. Therefore, the generation efficiency of the up-conversion light can be measured easily with fewer measurement times and under the same measurement condition.

The filter unit 61 includes a first filter that selectively attenuates the excitation light out of the excitation light and the up-conversion light, and a second filter that attenuates both the excitation light and the up-conversion light. Therefore, the filter unit 61 attenuates the light output from the light output portion 23 with both the first filter and the second filter, and thus, both the excitation light and the up-conversion light can be attenuated and the generation efficiency of the up-conversion light can be measured with high accuracy.

By the use of the filter set 60 including the filter unit 61 and the opening 63, the filter unit 61 and the opening 63 can be switched so that one of the filter unit and the opening can receive the light output from the light output portion 23, and thus, the measurement of the transmission spectrum of the filter and the measurement of the generation efficiency of the up-conversion light can be easily performed. In addition, the second filter is formed of the same material as the light-reflective material provided for the inner wall of the integrator 20, and therefore, the measurement of the generation efficiency of the up-conversion light is not easily influenced.

Embodiments of the present invention have been described, but the present invention is not limited to the above embodiments and various modifications are possible. Further, the present invention may be modified within the range not departing from the content described in claims and may be applied to others.

Figure 6:
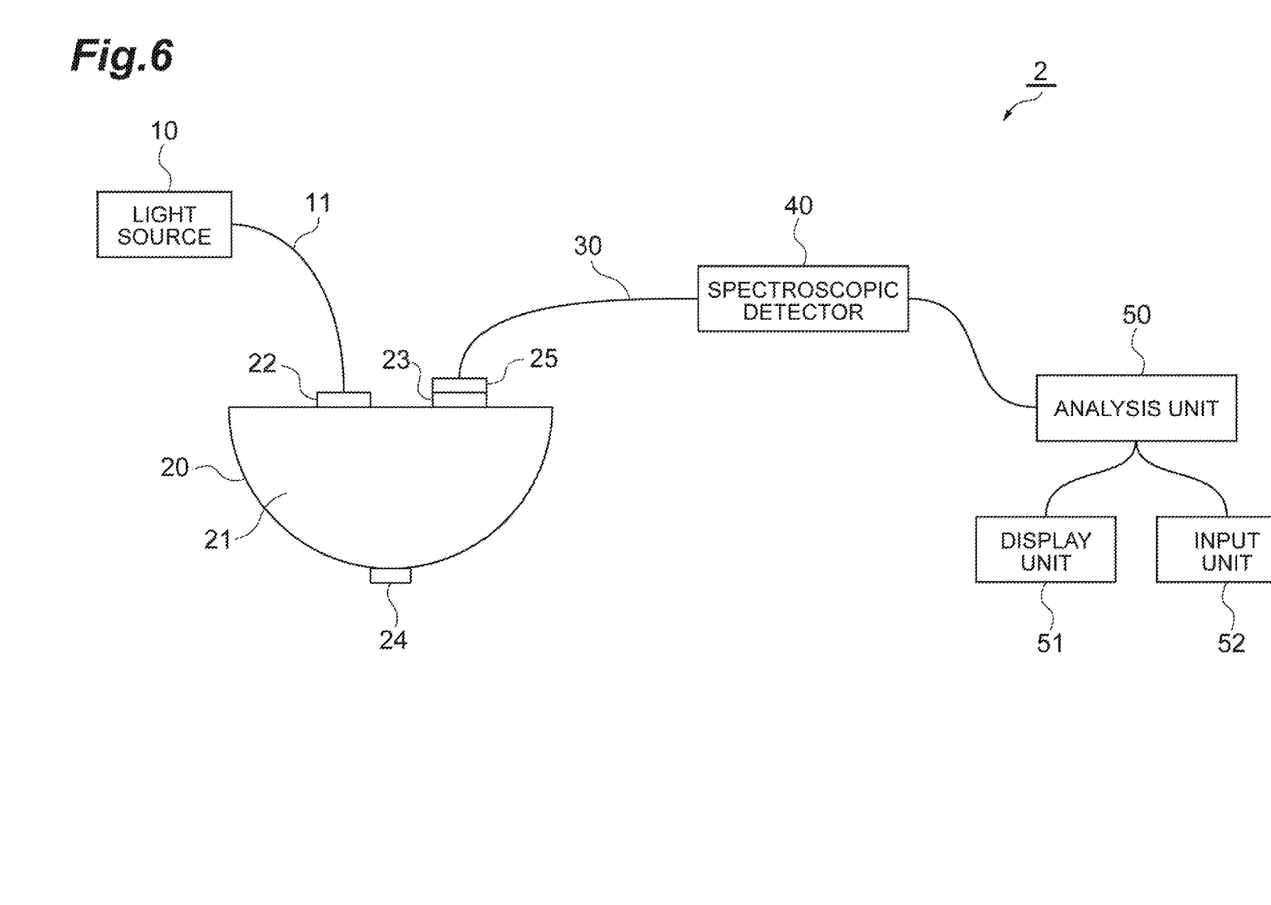
FIG. 6 is a diagram illustrating a configuration of a spectroscopic measurement apparatus 2.

For example, FIG. 6 is a diagram illustrating a configuration of a spectroscopic measurement apparatus 2. While the integrator 20 of the spectroscopic measurement apparatus 1 illustrated in FIG. 1 is the integrating sphere, the integrator 20 of the spectroscopic measurement apparatus 2 illustrated in FIG. 6 is the integrating hemisphere. The internal space 21 of the integrator 20 is the hemisphere whose inner wall of a hemispherical portion has a wall surface with high reflectance and excellent diffuseness, and whose planar portion is a flat mirror with high reflectance. The light input portion 22 and the light output portion 23 may be provided in any place in the hemispherical portion and the planar portion. Even when the spectroscopic measurement apparatus 2 is used, the generation efficiency of the up-conversion light can be measured easily like in the above-described case.

Instead of correcting the spectroscopic spectrum data on the basis of the transmission spectrum data and measuring the luminous efficiency on the basis of the corrected spectroscopic spectrum data, the luminous efficiency such as the quantum yield (internal quantum efficiency) or the external quantum efficiency may be obtained based on the spectroscopic spectrum data and then the luminous efficiency may be corrected on the basis of the transmission spectrum data. The spectroscopic spectrum data is not limited to the data representing the number of photons for each wavelength but may be the data representing the detection intensity for each wavelength. In this case, from the data representing the detection intensity for each wavelength, the numbers of photons $I_{S1}$ and $I_{R1}$ in the excitation light wavelength region and the numbers of photons $I_{S2}$ and $I_{R2}$ in the up-conversion light wavelength region may be obtained.

The spectroscopic measurement apparatus according to the embodiment is an apparatus for measuring luminous efficiency of a measurement object which outputs up-conversion light by input of excitation light, and the apparatus includes (1) an integrator including an internal space in which the measurement object is disposed, a light input portion for inputting the excitation light from outside to the internal space, and a light output portion for outputting light from the internal space to the outside; (2) a filter unit having a transmission spectrum in which an attenuation rate for the excitation light is larger than an attenuation rate for the up-conversion light, and for attenuating the light output from the light output portion in accordance with the transmission spectrum; (3) a spectroscopic detector for dispersing the light attenuated and output by the filter unit, and acquiring spectroscopic spectrum data; and (4) an analysis unit for analyzing the luminous efficiency of the measurement object on the basis of the transmission spectrum data and the spectroscopic spectrum data.

The spectroscopic measurement method according to the embodiment is a method for measuring luminous efficiency of a measurement object which outputs up-conversion light by input of excitation light (1) using an integrator including an internal space in which the measurement object is disposed, a light input portion for inputting the excitation light from outside to the internal space, and a light output portion for outputting light from the internal space to the outside, and the method includes (2) inputting the excitation light from the light input portion of the integrator to the internal space; (3) attenuating the light output from the light output portion in accordance with a transmission spectrum by a filter unit having the transmission spectrum in which an attenuation rate for the excitation light is larger than an attenuation rate for the up-conversion light; (4) dispersing the light attenuated and output by the filter unit and acquiring spectroscopic spectrum data by a spectroscopic detector; and (5) analyzing the luminous efficiency of the measurement object on the basis of the transmission spectrum data and the spectroscopic spectrum data by an analysis unit.

The spectroscopic measurement apparatus of the above configuration may further include a filter set including the filter unit and an opening, and the filter set may be configured to be switchable so that the filter unit or the opening receives the light output from the light output portion.

Further, in the spectroscopic measurement method of the above configuration, a filter set including the filter unit and an opening may be switched so that the filter unit or the opening receives the light output from the light output portion.

Further, in the spectroscopic measurement apparatus and method, the filter unit may include a first filter for selectively attenuating the excitation light out of the excitation light and the up-conversion light, and a second filter for attenuating both the excitation light and the up-conversion light. Further, in this case, it is preferable that the light output from the light output portion is attenuated by both the first filter and the second filter.

In the above configuration, the second filter may be an ND filter or may be formed of a light-reflective material. Further, the light-reflective material may be the same material as a light-reflective material provided for an inner wall of the integrator.

Further, in the above configuration, the first filter may be a short-pass filter or a band-pass filter.

Further, in the spectroscopic measurement apparatus, the analysis unit may correct the spectroscopic spectrum data on the basis of the transmission spectrum data, and analyze the luminous efficiency of the measurement object on the basis of the corrected spectroscopic spectrum data. Further, in the spectroscopic measurement method, by the analysis unit, the spectroscopic spectrum data may be corrected on the basis of the transmission spectrum data, and the luminous efficiency of the measurement object may be analyzed on the basis of the corrected spectroscopic spectrum data.

INDUSTRIAL APPLICABILITY

The present invention is applicable as a spectroscopic measurement apparatus and a spectroscopic measurement method that can easily measure the generation efficiency of the up-conversion light.

REFERENCE SIGNS LIST 1, 2—spectroscopic measurement apparatus, 10—light source, 11—input light guide, 20—integrator, 21—internal space, 22—light input portion, 23—light output portion, 24—sample attachment portion, 25—filter attachment portion, 30—output light guide, 40—-spectroscopic detector, 50—analysis unit, 51—display unit, 52—input unit, 60—filter set, 61—filter unit.

The invention claimed is:

1. A spectroscopic measurement apparatus for measuring luminous efficiency of a measurement object which outputs up-conversion light by input of excitation light, the apparatus comprising:
an integrator including an internal space in which the measurement object is disposed, a light input portion configured to input the excitation light from outside to the internal space, and a light output portion configured to output light from the internal space to the outside;
a filter unit having a transmission spectrum in which an attenuation rate for the excitation light is larger than an attenuation rate for the up-conversion light, and configured to attenuate the light output from the light output portion in accordance with the transmission spectrum;
a spectroscopic detector configured to disperse the light attenuated and output by the filter unit, and acquire spectroscopic spectrum data; and
an analysis unit configured to analyze the luminous efficiency of the measurement object on the basis of transmission spectrum data of the transmission spectrum of the filter unit and the spectroscopic spectrum data, wherein
the analysis unit is configured to correct the spectroscopic spectrum data on the basis of the transmission spectrum data, and analyze the luminous efficiency of the measurement object on the basis of the corrected spectroscopic spectrum data.

2. The spectroscopic measurement apparatus according to claim 1, further comprising a filter set including the filter unit and an opening, wherein the filter set is configured to be switchable so that the filter unit or the opening receives the light output from the light output portion.

3. The spectroscopic measurement apparatus according to claim 1, wherein the filter unit includes a first filter configured to selectively attenuate the excitation light out of the excitation light and the up-conversion light, and a second filter configured to attenuate both the excitation light and the up-conversion light, and the light output from the light output portion is attenuated by both the first filter and the second filter.

4. The spectroscopic measurement apparatus according to claim 3, wherein the second filter is an ND filter.

5. The spectroscopic measurement apparatus according to claim 3, wherein the second filter is formed of a light-reflective material.

6. The spectroscopic measurement apparatus according to claim 5, wherein the light-reflective material is the same material as a light-reflective material provided for an inner wall of the integrator.

7. The spectroscopic measurement apparatus according to claim 3, wherein the first filter is a short-pass filter or a band-pass filter.

8. A spectroscopic measurement method for measuring luminous efficiency of a measurement object which outputs up-conversion light by input of excitation light using an integrator including an internal space in which the measurement object is disposed, a light input portion configured to input the excitation light from outside to the internal space, and a light output portion configured to output light from the internal space to the outside, the method comprising:
inputting the excitation light from the light input portion of the integrator to the internal space;
attenuating the light output from the light output portion in accordance with a transmission spectrum by a filter unit having the transmission spectrum in which an attenuation rate for the excitation light is larger than an attenuation rate for the up-conversion light;
dispersing the light attenuated and output by the filter unit and acquiring spectroscopic spectrum data by a spectroscopic detector; and
analyzing the luminous efficiency of the measurement object on the basis of transmission spectrum data of the transmission spectrum of the filter unit and the spectroscopic spectrum data by an analysis unit, wherein
by the analysis unit, the spectroscopic spectrum data is corrected on the basis of the transmission spectrum data, and the luminous efficiency of the measurement object is analyzed on the basis of the corrected spectroscopic spectrum data.

9. The spectroscopic measurement method according to claim 8, wherein a filter set including the filter unit and an opening is switched so that the filter unit or the opening receives the light output from the light output portion.

10. The spectroscopic measurement method according to claim 8, wherein the filter unit includes a first filter configured to selectively attenuate the excitation light out of the excitation light and the up-conversion light, and a second filter configured to attenuate both the excitation light and the up-conversion light, and the light output from the light output portion is attenuated by both the first filter and the second filter.

11. The spectroscopic measurement method according to claim 10, wherein the second filter is an ND filter.

12. The spectroscopic measurement method according to claim 10, wherein the second filter is formed of a light-reflective material.

13. The spectroscopic measurement method according to claim 12, wherein the light-reflective material is the same material as a light-reflective material provided for an inner wall of the integrator.

14. The spectroscopic measurement method according to claim 10, wherein the first filter is a short-pass filter or a band-pass filter.

15. A spectroscopic measurement apparatus for measuring luminous efficiency of a measurement object which outputs up-conversion light by input of excitation light, the apparatus comprising:
an integrator including an internal space in which the measurement object is disposed, a light input portion configured to input the excitation light from outside to the internal space, and a light output portion configured to output light from the internal space to the outside;
a filter unit having a transmission spectrum in which an attenuation rate for the excitation light is larger than an attenuation rate for the up-conversion light, and configured to attenuate the light output from the light output portion in accordance with the transmission spectrum;
a spectroscopic detector configured to disperse the light attenuated and output by the filter unit, and acquire spectroscopic spectrum data; and
an analysis unit configured to analyze the luminous efficiency of the measurement object on the basis of transmission spectrum data of the transmission spectrum of the filter unit and the spectroscopic spectrum data, wherein
the filter unit includes a first filter configured to selectively attenuate the excitation light out of the excitation light and the up-conversion light, and a second filter configured to attenuate both the excitation light and the up-conversion light, and the light output from the light output portion is attenuated by both the first filter and the second filter, and
the second filter is formed of a light-reflective material.

16. A spectroscopic measurement apparatus for measuring luminous efficiency of a measurement object which outputs up-conversion light by input of excitation light, the apparatus comprising:
an integrator including an internal space in which the measurement object is disposed, a light input portion configured to input the excitation light from outside to the internal space, and a light output portion configured to output light from the internal space to the outside;
a filter unit having a transmission spectrum in which an attenuation rate for the excitation light is larger than an attenuation rate for the up-conversion light, and configured to attenuate the light output from the light output portion in accordance with the transmission spectrum;
a spectroscopic detector configured to disperse the light attenuated and output by the filter unit, and acquire spectroscopic spectrum data; and
an analysis unit configured to analyze the luminous efficiency of the measurement object on the basis of transmission spectrum data of the transmission spectrum of the filter unit and the spectroscopic spectrum data, wherein
the filter unit includes a first filter configured to selectively attenuate the excitation light out of the excitation light and the up-conversion light, and a second filter configured to attenuate both the excitation light and the up-conversion light, and the light output from the light output portion is attenuated by both the first filter and the second filter, and
the first filter is a short-pass filter or a band-pass filter.

17. A spectroscopic measurement method for measuring luminous efficiency of a measurement object which outputs up-conversion light by input of excitation light using an integrator including an internal space in which the measurement object is disposed, a light input portion configured to input the excitation light from outside to the internal space, and a light output portion configured to output light from the internal space to the outside, the method comprising:
inputting the excitation light from the light input portion of the integrator to the internal space;
attenuating the light output from the light output portion in accordance with a transmission spectrum by a filter unit having the transmission spectrum in which an attenuation rate for the excitation light is larger than an attenuation rate for the up-conversion light;
dispersing the light attenuated and output by the filter unit and acquiring spectroscopic spectrum data by a spectroscopic detector; and
analyzing the luminous efficiency of the measurement object on the basis of transmission spectrum data of the transmission spectrum of the filter unit and the spectroscopic spectrum data by an analysis unit, wherein
the filter unit includes a first filter configured to selectively attenuate the excitation light out of the excitation light and the up-conversion light, and a second filter configured to attenuate both the excitation light and the up-conversion light, and the light output from the light output portion is attenuated by both the first filter and the second filter, and
the second filter is formed of a light-reflective material.

18. A spectroscopic measurement method for measuring luminous efficiency of a measurement object which outputs up-conversion light by input of excitation light using an integrator including an internal space in which the measurement object is disposed, a light input portion configured to input the excitation light from outside to the internal space, and a light output portion configured to output light from the internal space to the outside, the method comprising:
inputting the excitation light from the light input portion of the integrator to the internal space;
attenuating the light output from the light output portion in accordance with a transmission spectrum by a filter unit having the transmission spectrum in which an attenuation rate for the excitation light is larger than an attenuation rate for the up-conversion light;
dispersing the light attenuated and output by the filter unit and acquiring spectroscopic spectrum data by a spectroscopic detector; and
analyzing the luminous efficiency of the measurement object on the basis of transmission spectrum data of the transmission spectrum of the filter unit and the spectroscopic spectrum data by an analysis unit, wherein the filter unit includes a first filter configured to selectively attenuate the excitation light out of the excitation light and the up-conversion light, and a second filter configured to attenuate both the excitation light and the up-conversion light, and the light output from the light output portion is attenuated by both the first filter and the second filter, and the first filter is a short-pass filter or a band-pass filter.

* * * * *